US00PP08409P

United States Patent [19]

Trees

[11] Patent Number: Plant 8,409

[45] Date of Patent: Oct. 5, 1993

[54] NEW GUINEA IMPATIENS NAMED BSR-152 DARK PINK

[75] Inventor: Scott C. Trees, Arroyo Grande, Calif.

[73] Assignee: George J. Ball, Inc., West Chicago, Ill.

[21] Appl. No.: 911,539

[22] Filed: Jul. 10, 1992

[51] Int. Cl.[5] ..... A01H 5/00

[52] U.S. Cl. ..... Plt./87.6

[58] Field of Search ..... Plt./87.6

*Primary Examiner*—James R. Feyrer

*Attorney, Agent, or Firm*—Burns, Doane, Swecker & Mathis

[57] ABSTRACT

A new and distinct New Guinea Impatiens cultivar named BSR-152 Dark Pink is provided. This new cultivar was the result of a controlled breeding program wherein the Caligo cultivar (U.S. Plant Pat. No. 6,682) was pollinated by the Eurema cultivar (U.S. Plant Pat. No. 6,681). The new cultivar forms attractive very large pink blossoms combined with a strong basal branching character and a compact upright mounded growth habit and can be readily distinguished from the Delias cultivar (U.S. Plant patent application pending).

1 Drawing Sheet

SUMMARY OF THE INVENTION

The present invention comprises a new and distinctive Impatiens plant, botanically known as New Guinea Impatiens, and hereafter referred to by the cultivar name BSR-152 Dark Pink.

The new cultivar is the product of a planned breeding program. More specifically, the breeding program which resulted in the production of the new cultivar was carried out in a controlled environment during 1989 at Santa Maria, Calif., U.S.A. The female parent (i.e., the seed parent) was the Caligo cultivar (U.S. Plant Pat. No. 6,682) which exhibits blush pink blossoms with dark bronze foliage. The male parent (i.e., the pollen parent) was the Eurema cultivar (U.S. Plant Pat. No. 6,681) which exhibits coral orange blossoms with variegated dark green foliage. The parentage of the new cultivar can be summarized as follows:

Caligo × Eurema.

The seeds resulting from the above pollination were sown and plantlets were obtained which were physically and biologically different from each other. Selective study resulted in the identification of a single plant of the new cultivar. This plant had dark pink blossoms and initially was designated BSR-152.

It was found that the cultivar of the present invention:

(a) exhibits attractive very large dark pink blossoms which commonly measure approximately 6.25 cm. in diameter and approximately 5.5 cm. in length,
(b) exhibits a strong basal branching character, and
(c) exhibits a compact upright mounded growth habit.

Asexual reproduction of the new cultivar by terminal or stem cuttings taken during February, 1990 at Santa Maria, Calif., has demonstrated that the characteristics of the new cultivar as herein described are firmly fixed and are retained through successive generations of such asexual propagation.

The BSR-152 Dark Pink cultivar has not been observed under all possible environmental conditions to date. Accordingly, it is possible that the phenotype may vary somewhat with variations in the environment, such as temperature, light intensity, and day length.

When the new cultivar of the present invention is compared to the Delias cultivar (U.S. Plant patent application pending), it is found that the new variety exhibits a compact upright mounded growth habit whereas the Delias cultivar exhibits a more spreading mounded growth habit.

When plant material of the BSR-152 Dark Pink cultivar is subjected to standard random amplified polymorphic DNA marker analysis (RAPD) using polymerase chain reaction (PCR) and a known unique set of DNA primers, it is found to exhibit a different fingerprint map when compared to that of the Delias cultivar which confirms its genetic distinctiveness.

Plants of the new cultivar will be marketed under the Celebration trademark by George J. Ball, Inc.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at Arroyo Grande, Calif., U.S.A.

DETAILED DESCRIPTION

The chart used in the identification of colors described herein is The R.H.S. Colour Chart of The Royal Horticultural Society, London, England. The color values were determined during the first week of January, 1992. The readings were taken at 1:50 p.m. under 2,000 footcandles at Arroyo Grande, Calif., U.S.A. The plants were produced from cuttings taken from stock plants and were grown under standard greenhouse conditions comparable to those used in commercial practice while utilizing a soilless growth medium and maintaining temperatures of approximately 72° F. during the day and approximately 65° F. during the night.

Propagation:

*Type cutting.*—Terminal tip.

*Time to initiate roots.*—Approximately 14 to 21 days with the shorter times generally being experienced in the summer and the longer times in the winter.

*Rooting habit.*—Fibrous and branching.

Plant description:

*Form.*—Strong basal branching.

*Habit of growth.*—Compact and upright mounded. A mature plant commonly measures approximately 12 inches in height and approximately 15 inches in width.

*Foliage.*—The configuration is narrow and lanceolate. The leaves of the BSR-152 Dark Pink cultivar measure approximately 12 cm.×3.5 cm. while those of the Delias cultivar measure approximately 11.5 cm.×3.0 cm. The foliage of the BSR-152 Dark Pink cultivar is Green Group 135A (abaxial) and Green Group 132C with veins of Red Group 53A (adaxial). This can be compared to Green Group 141B (abaxial) and Green Group 141C with veins of Red Group 46A (adaxial) for the Delias cultivar. The stem color is Red Group 53A while that of the Delias cultivar is Red Group 46A.

Flower description:

*Flowering habit.*—Freely flowering.

*Natural flowering season.*—Year-round in greenhouse environment.

*Flowers borne.*—Above foliage, arising from leaf axils.

*Flower color.*—Red Group 58C (abaxial) and Red-Purple Group 66C (adaxial). This can be compared to Red-Purple Group 70C (abaxial and adaxial) for the Delias cultivar.

*Quantity of flowers.*—Approximately 5 to 10 per stem.

*Number of petals.*—Five.

*Flower diameter.*—Approximately 6.25 cm. which can be compared to approximately 5.5 cm. for the Delias cultivar.

*Nectary length.*—Approximately 5.5 cm. which can be compared to approximately 5.0 cm. for the Delias cultivar.

*Nectary color.*—Red Group 53B which can be compared to Red-Purple Group 60B for the Delias cultivar.

*Reproductive organs.*—The anthers are fused together forming one organ that surrounds the pistil. Generally, the anthers shed pollen prior to the stigma becoming receptive. The pollen color is cream-white, White Group 155D. The stigma color is Red-Purple Group 63B and can be compared to White Group 155C exhibited by the Delias cultivar. The ovary color is Yellow-Green Group 144A and can be compared to Green Group 141A exhibited by the Delias cultivar.

I claim:

1. A new and distinct cultivar of New Guinea Impatiens named BSR-152 Dark Pink, substantially as herein shown and described, which:

(a) exhibits attractive very large dark pink blossoms which commonly measure approximately 6.25 cm. in diameter and approximately 5.5 cm. in length, (b) exhibits a strong basal branching character, and (c) exhibits a compact upright mounded growth habit.

* * * * *

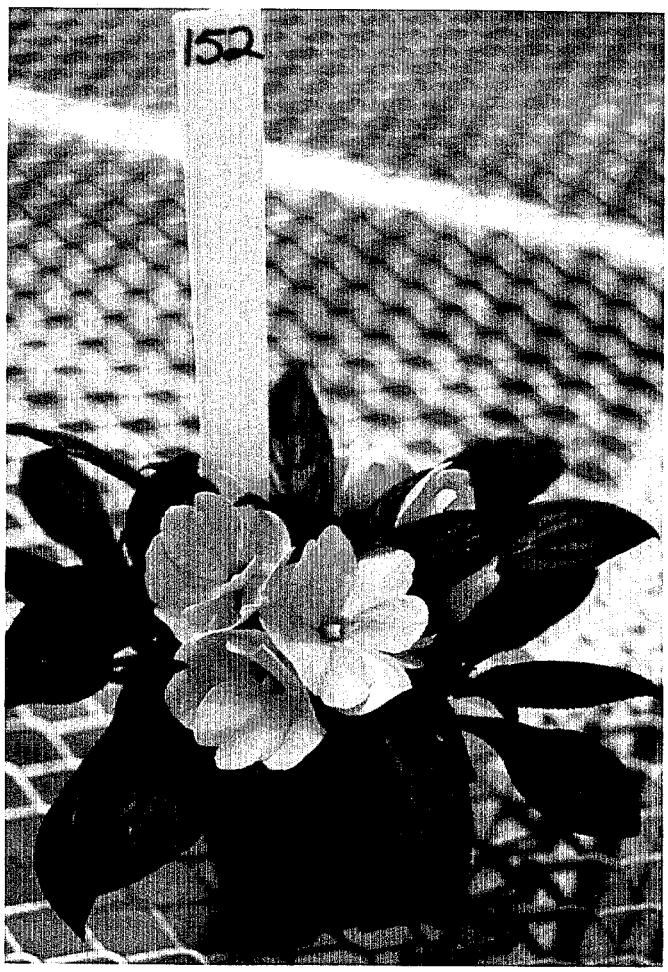
152